United States Patent
Guibal

(10) Patent No.: US 11,796,519 B2
(45) Date of Patent: Oct. 24, 2023

(54) PROCESS FOR POLYSORBATE QUANTIFICATION IN A SAMPLE INVOLVING LC-MS WITH AN INTERNAL STANDARD

(71) Applicant: SANOFI, Paris (FR)

(72) Inventor: Pierre Guibal, Paris (FR)

(73) Assignee: SANOFI, Paris (FR)

( * ) Notice: Subject to any disclaimer, the term of this patent is extended or adjusted under 35 U.S.C. 154(b) by 119 days.

(21) Appl. No.: 17/432,595

(22) PCT Filed: Feb. 27, 2020

(86) PCT No.: PCT/EP2020/055191
§ 371 (c)(1),
(2) Date: Aug. 20, 2021

(87) PCT Pub. No.: WO2020/174064
PCT Pub. Date: Sep. 3, 2020

(65) Prior Publication Data
US 2022/0120720 A1 Apr. 21, 2022

(30) Foreign Application Priority Data
Feb. 27, 2019 (EP) .................................. 19305232

(51) Int. Cl.
*G01N 30/72* (2006.01)
*G01N 30/62* (2006.01)

(52) U.S. Cl.
CPC ... *G01N 30/7233* (2013.01); *G01N 2030/626* (2013.01)

(58) Field of Classification Search
CPC ......... G01N 30/7233; G01N 2030/626; G01N 2560/00; G01N 33/6854
See application file for complete search history.

(56) References Cited

U.S. PATENT DOCUMENTS

| | | | |
|---|---|---|---|
| 2014/0249054 A1* | 9/2014 | Gelb | C12Q 1/44 435/19 |
| 2015/0129766 A1* | 5/2015 | Gbaguidi | G01N 21/55 250/340 |
| 2021/0268073 A1* | 9/2021 | Xiao | G01N 33/54306 |

FOREIGN PATENT DOCUMENTS

WO    WO 2013/175312 A1    11/2013

OTHER PUBLICATIONS

Borisov et al., "Oxidative Degradation of Polysorbate Surfactants Studied by Liquid Chromatography-Mass Spectrometry", Journal of Pharmaceutical Sciences, 2018, 104: 1005-1018.
Borisov et al., "Toward Understanding Molecular Heterogeneity of Polysorbates by Application of Liquid Chromatography-Mass Spectrometry with Computer-Aided Data Analysis", Analytical Chemistry, 2011, 83: 3934-3942.
Extended European Search Report for European Patent Application No. 19305232.1, dated May 15, 2019.
(Continued)

*Primary Examiner* — David J Bolduc
(74) *Attorney, Agent, or Firm* — LATHROP GPM LLP; James H. Velema; Judith L. Stone-Hulslander

(57) ABSTRACT

The present application concerns a process for quantifying polysorbates in a sample by implementing a LC-MS analysis with an internal standard, and the process for monitoring degradation of polysorbates in such sample.

13 Claims, 10 Drawing Sheets

(56) References Cited

OTHER PUBLICATIONS

Hall et al., "Polysorbates 20 and 80 Degradation by Group XV Lysomal Phospholipase $A_2$ Isomer X1 in Monoclonal Antibody Formulations", Journal of Pharmaceutical Sciences, 2016, 105: 1633-1642.

International Search Report for PCT International Patent Application No. PCT/EP2020/055191, dated Apr. 24, 2020.

Martos et al., "Trends on Analytical Characterization of Polysorbates and Their Degradation Products in Biopharmaceutical Formulations", Journal of Pharmaceutical Sciences, 2017, 106: 1722-1735.

Snelling et al., "Characterization of Complex Polysorbate Formulations by Means of Shape-Selective Mass Spectrometry", Analytical Chemistry, 2012, 84: 6521-6529.

Zhang et al., "Dual Effect of Histidine on Polysorbate 20 Stability: Mechanistic Studies", Pharmaceutical Research, 2018, 35: 33.

\* cited by examiner

PROCESS FOR POLYSORBATE QUANTIFICATION IN A SAMPLE INVOLVING LC-MS WITH AN INTERNAL STANDARD

RELATED APPLICATIONS

This application is a 35 U.S.C. § 371 filing of International Patent Application No. PCT/EP2020/055191, filed Feb. 27, 2020, which claims priority to European Patent Application No. 19305232.1, filed Feb. 27, 2019, the entire disclosures of which are hereby incorporated herein by reference.

The present invention concerns analytical methods for quantifying polysorbates in biotherapeutics samples. Polysorbates, such as PS80, are the most commonly used surfactants in biotherapeutics formulation.

Polysorbates are amphiphilic non-ionic surfactants commonly used in biopharmaceuticals formulations. Their main role is to protect protein and monoclonal antibodies (mAb) against interfacially induced aggregation. Polysorbates, such as PS80 are a heterogenic mixture of more than 1500 molecules covering a wide range of physico-chemical properties and including a variety of fatty acids. PS80 is defined as a polyoxyethylene sorbitan monooleate but due to its synthesis process, it is a heterogenic mixture, also known to be prone to autoxidation and enzymatic hydrolysis of the esterified fatty acids. Major source of PS80 heterogeneity can be attributed to the ester bond and several fatty acids involved in it. Indeed, several works reported the presence of large amounts (up to 34.1%) of di-esters and sometimes higher order esters (Borisov et al Pharm. Biotechnol. 2015, 104, 1005-1018). This complexity represents a tremendous challenge for PS80 quantification and degradation monitoring.

In a recent review (Martos et al. J. Pharm. Sci. 2017, 106, 1722-1735), different methods for PS80 monitoring are described. Methods reported are based on different detection technologies mostly hyphenated with liquid chromatography (LC). Amongst the mentioned methods, those which are able to quantify PS80 are not sensitive to all kinds of PS80 degradation. For example, methods based on mixed-mode liquid chromatography with ELSD or CAD are suitable for PS80 quantification but are not the most sensitive methods in case of PS80 degradation. Methods based on mass spectrometry (MS) are often used for PS80 characterization but not for PS80 quantification and monitoring in a quality control (QC) environment. Recent advancements on liquid chromatography mass spectrometry (LC-MS) characterization of PS80 are based on characteristic signal of dioxolanylium ion (Borisov et al. *Anal. Chem.* 2011, 83, 3934-3942). Reported use of these characteristic signals mentioned their usefulness for interpretation and identification of PS80 species and especially fatty acids composition. It was also used for structural elucidation of PS80 oxidative byproducts (Borisov et al., 2015, supra). So far, these signals have not been used for PS80 quantification. Only relative or semi quantitative information has been retrieved from the obtained chromatograms (Borisov et al, 2011, supra).

It is therefore still desirable to provide an efficient and robust method to allow the polysorbates quantification in a single analysis.

According to an object, the present invention provides a process for quantifying at least one polysorbate derivative in a sample, said process comprising:
The step of performing a LC-MS analysis of said sample based on the signal of the dioxolanylium ion;
The step of performing an internal calibration with an internal standard of said polysorbate.

Although use of an internal standard (IS) is a well-known practice in chromatography and mass spectrometry, use of IS for polysorbates quantification has never been reported. By using an internal standard (IS), linearity, repeatability, accuracy and therefore quantification were improved.

One key feature of the method is to use an internal standard for internal calibration purpose in order to avoid issue with matrix effects. Typically, this internal standard has a similar chemical structure and undergoes the same in source fragmentation as surrogate of intact polysorbate. According to the invention, the method relies on characteristic dioxolanylium ions of fatty acids ester generated by in source dissociation.

By using a carefully chosen internal standard, the method allows quantification of polysorbates in a typical mAb formulation.

According to an embodiment, polysorbates are a mixture of compounds of formula (I):

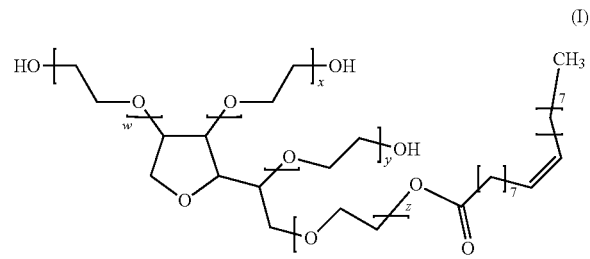

(I)

where w, x, y and z identical or different, independently represent the number of polyethylene glycol units in formula (I), and are different from 0.

According to an embodiment, w+x+y+z=20 where the polysorbate is in particular PS20 or PS80.

According to an embodiment, said polysorbate is PS20 or PS80. PS20 and PS80 are commercially available (in particular form Seppic—Puteaux, France)).

According to an embodiment, said LC-MS analysis involves a single quadrupole mass detector such as QDa® (available from Waters). By using in source fragmentation in a QDa mass detector, dioxolanylium ions are generated from the polysorbate. QDa is able to perform multiple single ion recording (SIR) signals in parallel in both positive and negative ionization mode in the same analytical run. This allows to quantify intact polysorbate, to look for characteristic polysorbate oxidative byproducts as well as to quantify free oleic acid, byproduct of polysorbate hydrolysis. Typically, a minimum of four SIR signals were followed in the case of PS80: one for dioxolanylium ion of oleate ester, specific ion of intact PS80, one for dioxolanylium ion of IS, one for free oleic acid in negative ionization mode (major byproducts of PS80 hydrolysis), one for dioxolanylium ion of oxidized oleate ester (major byproducts of oxidized PS80. Other signals may be recorded for information purpose.

According to an embodiment, the process allows the follow up of SIR signals relative to byproducts of PS80 degradation: oleic acid (SIR negative m/z 281.3) in case of hydrolysis and oxidized oleate ester (SIR positive m/z 325.3) in case of oxidation.

This new method allows getting at least the same level of information in only one analysis, thus reducing time devoted to analysis of PS80. Information gathered by this method is much easier to understand as the analytes are really specific of either intact PS80 or marker of degraded PS80.

Therefore, according to an embodiment, the process also includes the step of detecting the oxidation and/or hydrolysis of said polysorbate. Contrary to the existing methods, the present process allows to quantify PS80 in a formulation whatever degradation occurred (either oxidation or hydrolysis) or adsorption that could diminish the overall concentration of the PS80 compounds.

FIG. 2(b) illustrates SIR signals at m/z 309.3 for quantification of intact PS80. According to an embodiment, the method can quantify intact PS80 by using a suitable surrogate sensitive to both PS80 oxidation and PS80 hydrolysis. Monoesters are more sensitive to degradation and may be used as a surrogate for polysorbates quantification. According to an embodiment, said specific surrogate of intact polysorbates may be monoesters. For PS80, the surrogate is the compound identified as peak 2.1 in FIG. 2(b). Typically, depending on the experimental conditions, this peak has a retention time comprised between 6 and 7 min; more specifically, in the experimental conditions described below in the experimental part, the peak has a retention time comprised between 6.85 and 6.95, more particularly about 6.9 min. Using this surrogate, the use of this method is relevant for intact PS80 quantification in case of degradation by hydrolysis or oxidation. No previously published method is able to do so.

As used herein, "internal standard" refers to a chemical compound that is added in a constant amount to samples, the blank and calibration standards in a chemical analysis. This compound can then be used for calibration by plotting the ratio of the polysorbate signal to the internal standard signal as a function of the polysorbate concentration of the standards. The internal standard is a compound that is generally very similar, but not identical to the polysorbate in the samples, as the effects of sample preparation should, relative to the amount of each species, be the same for the signal from the internal standard as for the signal(s) from the species of interest in the ideal case. The internal standard used needs generally to provide a signal that is similar to the polysorbate signal in most ways but sufficiently different so that the two signals are readily distinguishable by the instrument.

The internal standard should typically be similar in structure to the analyte of interest, have a similar retention time compared to the analyte of interest, and should undergo similar in source fragmentation. It must also be stable and must not interfere with the sample components.

According to an embodiment, an internal standard (IS) may be chosen compounds having a polyethyleneglycol chain esterified with one or several carboxylic acid, so as to have similar physico-chemical properties as the polysorbate. Typically, the carboxylic acid part needs to be different from fatty acids present in polysorbate mixture.

According to an embodiment, the internal standard is an ethoxylated fatty acid of formula (I):

(I)

wherein:

represents a fatty acid residue
where R represents a C3-C24 linear or branched saturated alkyl;
R' is H or

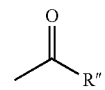

where R" represents a C3-C24 linear or branched saturated alkyl; and n is defined as the number of PEG (polyethyleneglycol) units in the general formula (I), it being understood that the compound of formula (I) is in the form of a mixture of one or more compounds of formula (I) with n identical or different being comprised between 1 and 100;
and the mixtures thereof.

According to an embodiment, n is an integer comprised between 1 and 100.

According to an embodiment, said internal standard is chosen from:

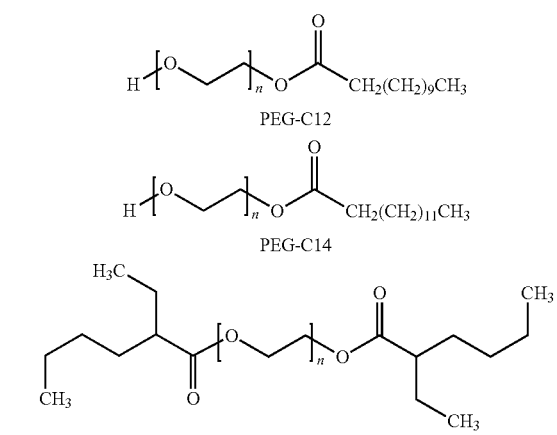

Poly(ethylene glycol)bis(2-ethylhexanoate)
where n defined as above being comprised between 1 and 100.

More particularly, the internal standard is polyethyleneglycol monolaurate (hereafter called PEG-C12) or polyethyleneglycol monomyristate (hereafter called PEG-C14); still more particularly:

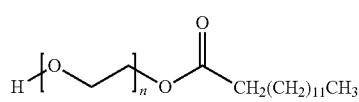

(polyethylene glycol myristate, PEG-C14).

PEG-C12 and Poly(ethylene glycol)bis(2-ethylhexanoate) are commercially available from Sigma-Aldrich (Saint Quentin Fallavier, France), and PEG-C14 is used as a component present in PEG-C12.

In the case of PEG-C12, n may be such that the average molecular weight is comprised between 300 and 600 g/mol, typically about 400 g/mol.

In the case of Poly(ethylene glycol)bis(2-ethylhexanoate), n may be such that the average molecular weight is comprised between 400 and 700 g/mol, typically about 650 g/mol. PEG-C14 may be isolated from PEG-C12, or can be used via PEG-C12 as a component present in PEG-C12.

It was found that the detection of the polysorbate mono and higher order ester and free oleic acid, and the sensitivity for the polysorbate and free oleic acid can be tuned with adjustments of the mobile phase and/or cone voltage.

According to an embodiment, the mobile phase of the LC-MS phase comprises a gradient of formic acid. Typically, the mobile phase is a ternary mobile phase comprising water, an organic solvent such as acetonitrile or isopropanol and an acid, such as formic acid or acetic acid. Typically, the mobile phase is made of water, acetonitrile and formic acid, with a gradient of acetonitrile and formic acid, typically with a formic acid gradient ranging from 0.01 to 0.1%. Generally, the composition of the eluting phase varies from an initial composition comprising 80-90% water, 10-20% acetonitrile and 0.01-0.05% formic acid towards a final composition comprising 0-10% water, 90-99.9% acetonitrile and 0.05-0.1% formic acid (in parts).

The cone voltage may induce in source fragmentation. Generally, the cone voltage is lower than 100 V, preferably lower than 70 V. Typically, a cone voltage (CV) different for the polysorbate and oleic acid may be used. As an illustration, CV 50 for PS80 and CV 15 for oleic acid may be used for achieving a higher sensitivity for PS80 and free oleic acid.

According to an embodiment, the process comprises the initial step of adding the internal standard to the sample. The method may also comprise the step of treating the sample for precipitating the proteins that may be comprised therein. Said treatment may comprise the addition of acetonitrile to the sample and/or centrifugation of said sample.

According to an embodiment, said sample is a biopharmaceutical formulation.

As used herein, a biopharmaceutical formulation is a pharmaceutical composition comprising at least one biological product, such as protein. Accordingly, said sample may comprise at least one therapeutic protein or biotherapeutic or Biologic, such as monoclonal antibody (mAb) or a fragment thereof, single-chain variable fragment (scFv), single-domain antibody (VHH antibody, i.e. nanobody), antibody drug conjugate, bispecific antibody, trispecific antibody.

According to another object, the present invention also concerns a process of monitoring the degradation of at least one polysorbate in a sample. Said process comprises implementing the process of quantifying said polysorbates according to the invention.

FIGURES

FIG. 1 summarizes PS80 theoretical structure and degradation pathways.

FIG. 2 shows the intensity (in arbitrary units) versus the retention time (in minutes). It illustrates the representative total ion current (TIC) profile of PS80 with peaks labeled as 1—non esterified species, 2—mono esters and 3—higher order esters (a), single ion recording (SIR) for m/z 309.3 indicating the elution of oleate species with peaks labeled as 2.1—POE sorbitan monooleate 2.2—POE isosorbide monooleate and 2.3—POE monooleate (b) and SIR for m/z 283.3 indicating the elution of palmitate species (c).

Figure 5:
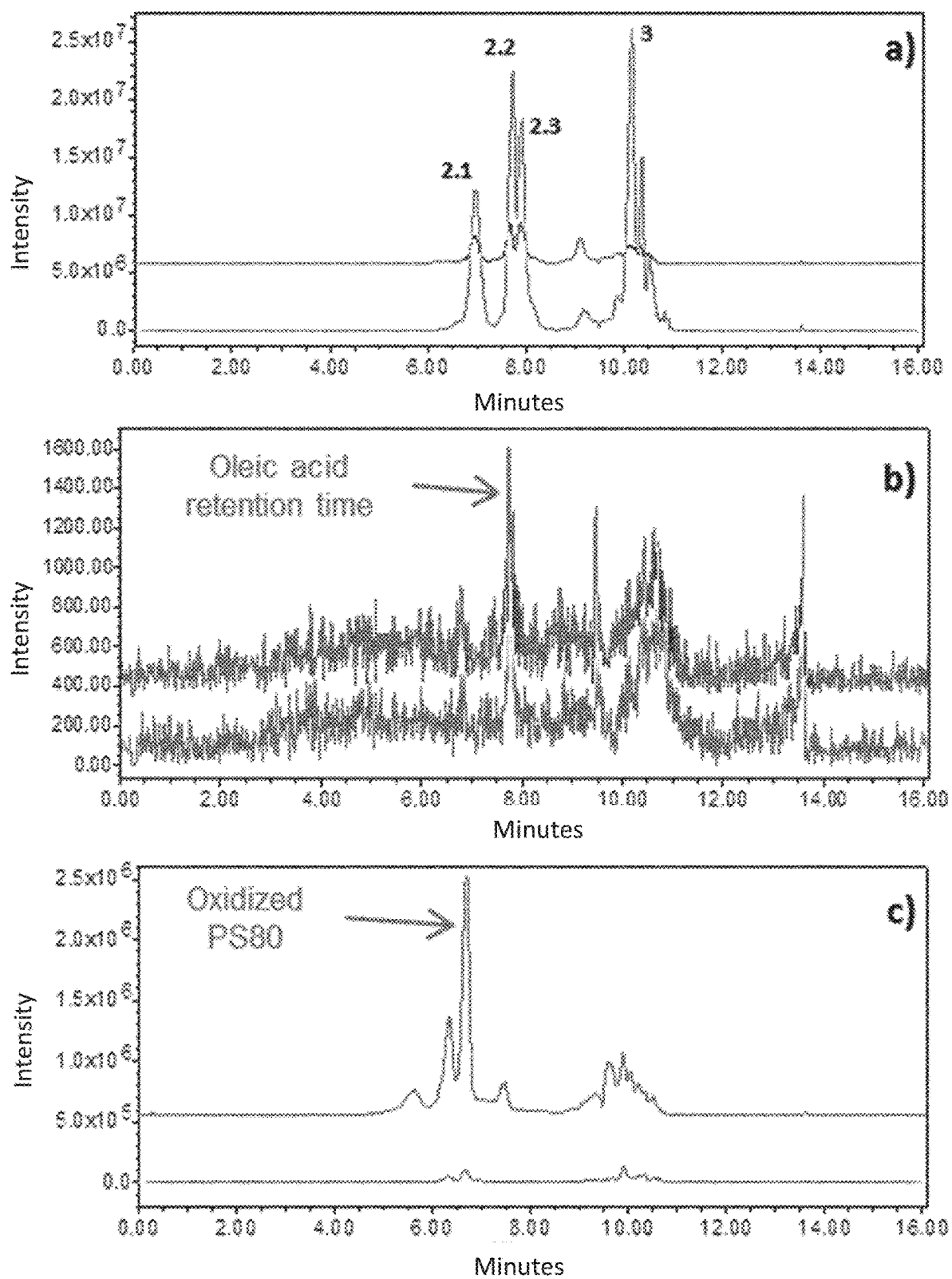

FIG. 5 illustrates representative chromatograms of a differential diagnosis of PS80 degradation in thermally stressed (top chromatogram) and unstressed (bottom chromatogram) samples. PS80 oleate subspecies are decreased in thermally stressed sample (a—pos m/z 309.3). No increase of oleic acid is observed (b—neg m/z 281.3) and oxidized byproducts increased drastically (c—pos m/z 325.3).

Figure 6:
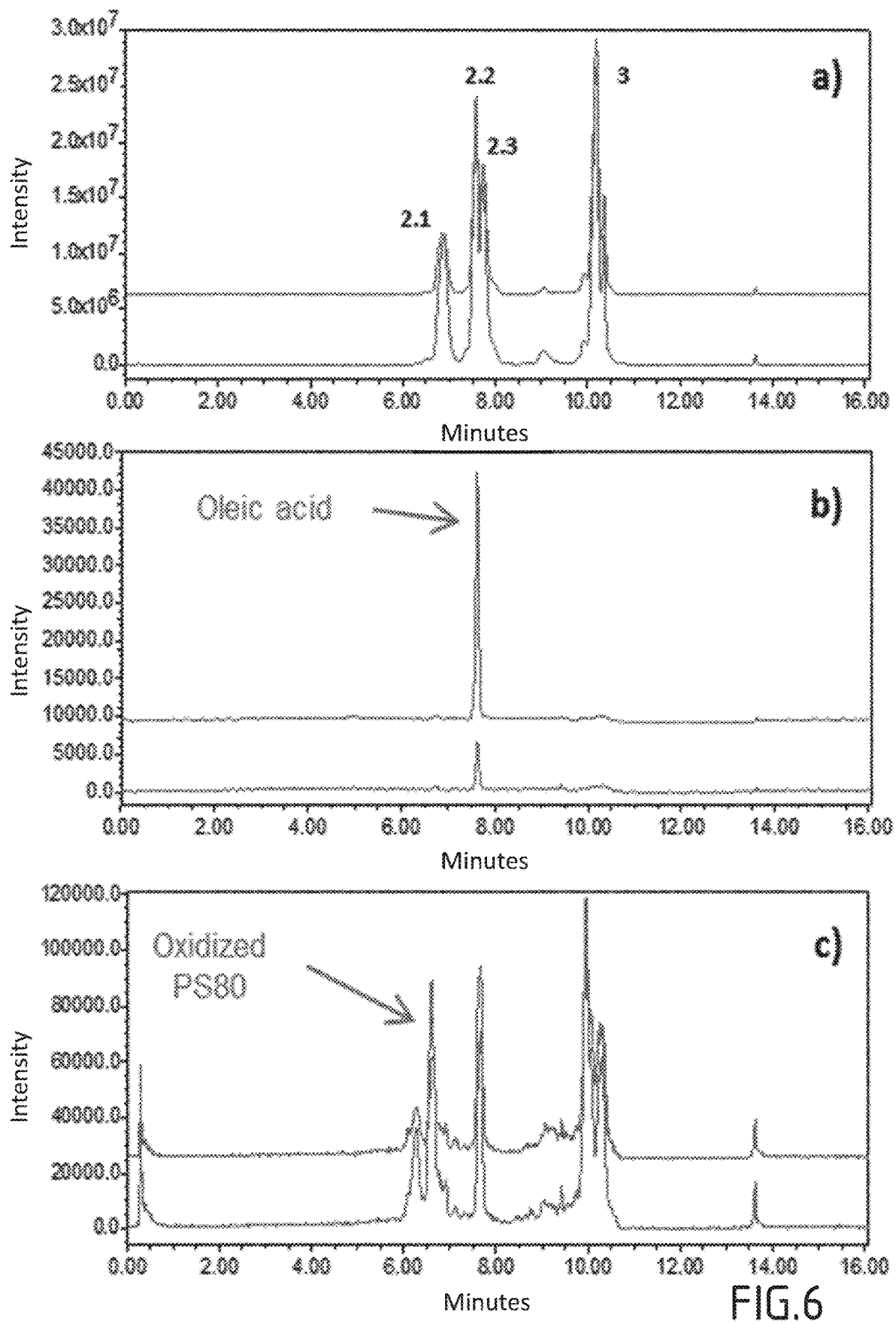

FIG. 6 illustrates representative chromatograms of a differential diagnosis of PS80 degradation in two different batches A (top chromatogram) or B (bottom chromatogram). PS80 oleate subspecies are decreased in batch A sample (a—pos m/z 309.3). Great increase of oleic acid is observed (b—neg m/z 281.3) and oxidized byproducts are no different in the two batches (c—pos m/z 325.3).

Figure 7:
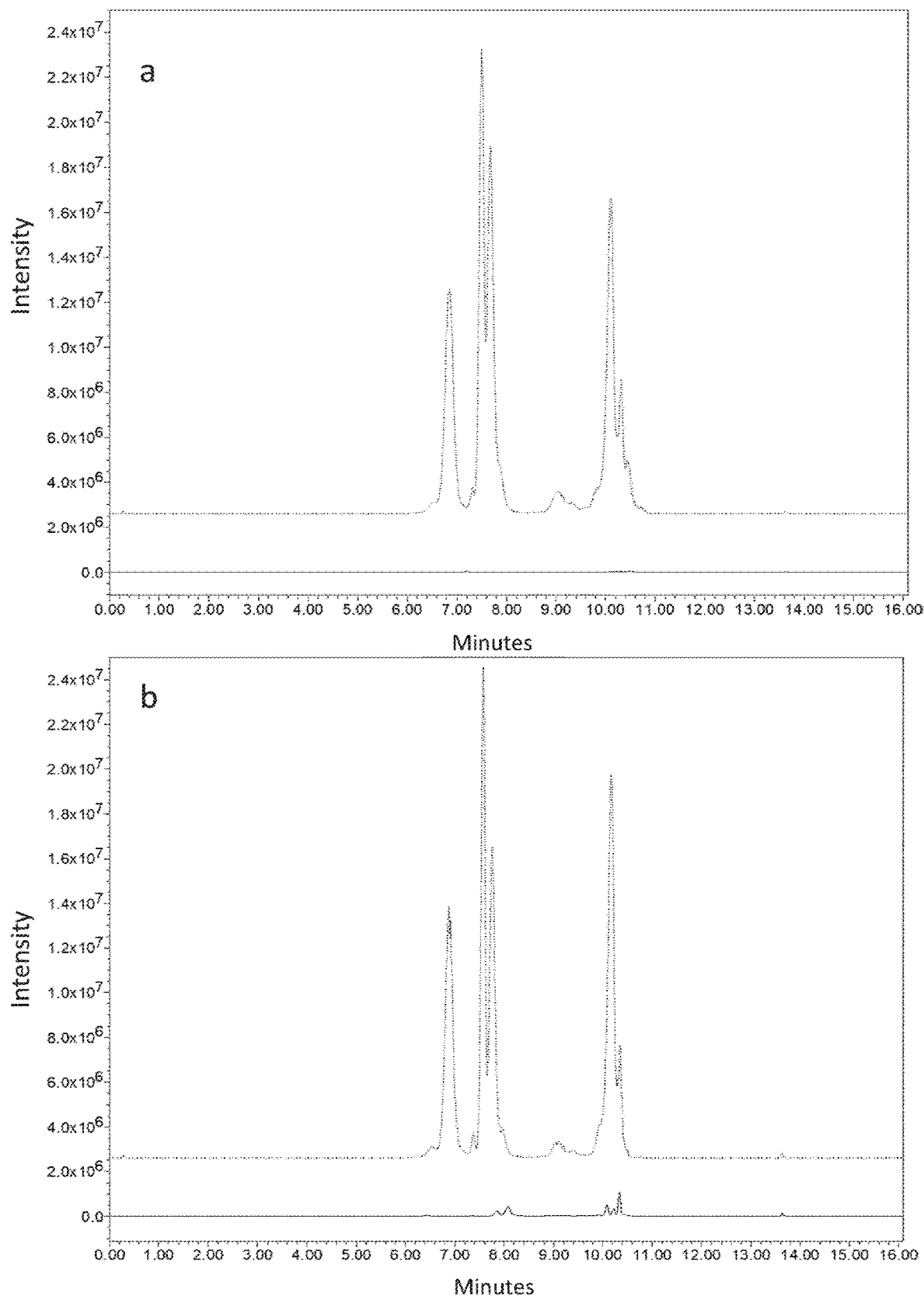

FIG. 7 illustrates the SIR signals in positive ionization mode at 309.3 m/z for PS80 sample at 50 µg/mL (dotted line) and internal standard (solid line) for PEG bis C8 (a) and PEG C12 and PEG C14 (b).

Figure 8:
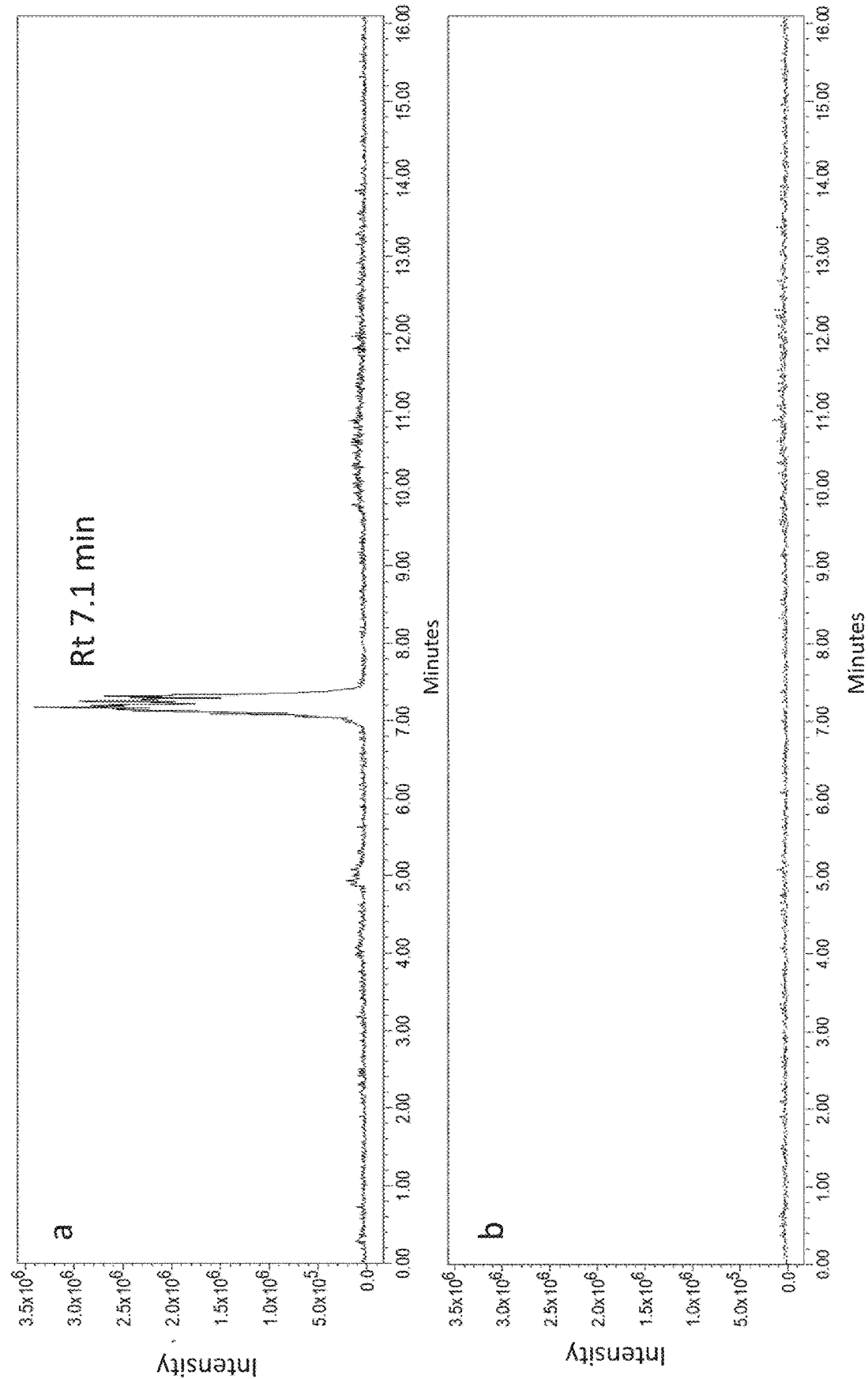

FIG. 8 is an extracted ion chromatogram in positive ionization mode at 171 m/z specific signal of PEG bis C8 for PS80 sample (dotted line—panel b) and PEG bis C8 (solid line—panel a). Retention time (Rt) of peak used as internal standard is given.

Figure 9:
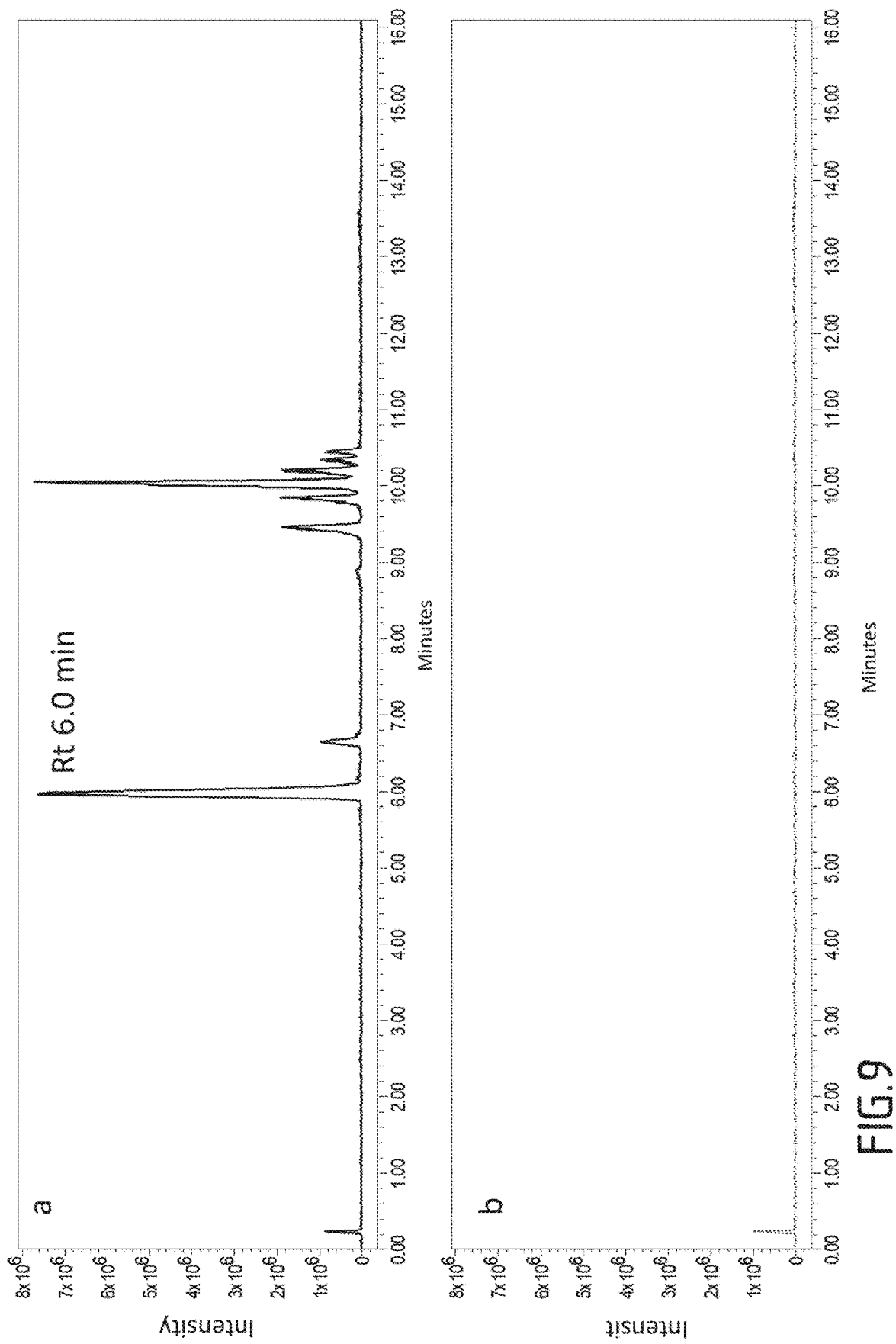

FIG. 9 is an extracted ion chromatogram in positive ionization mode at 227.3 m/z specific signal of PEG C12 for PS80 sample (dotted line—panel b) and PEG bis C8 (solid line—panel a). Retention time (Rt) of peak used as internal standard is given.

Figure 10:
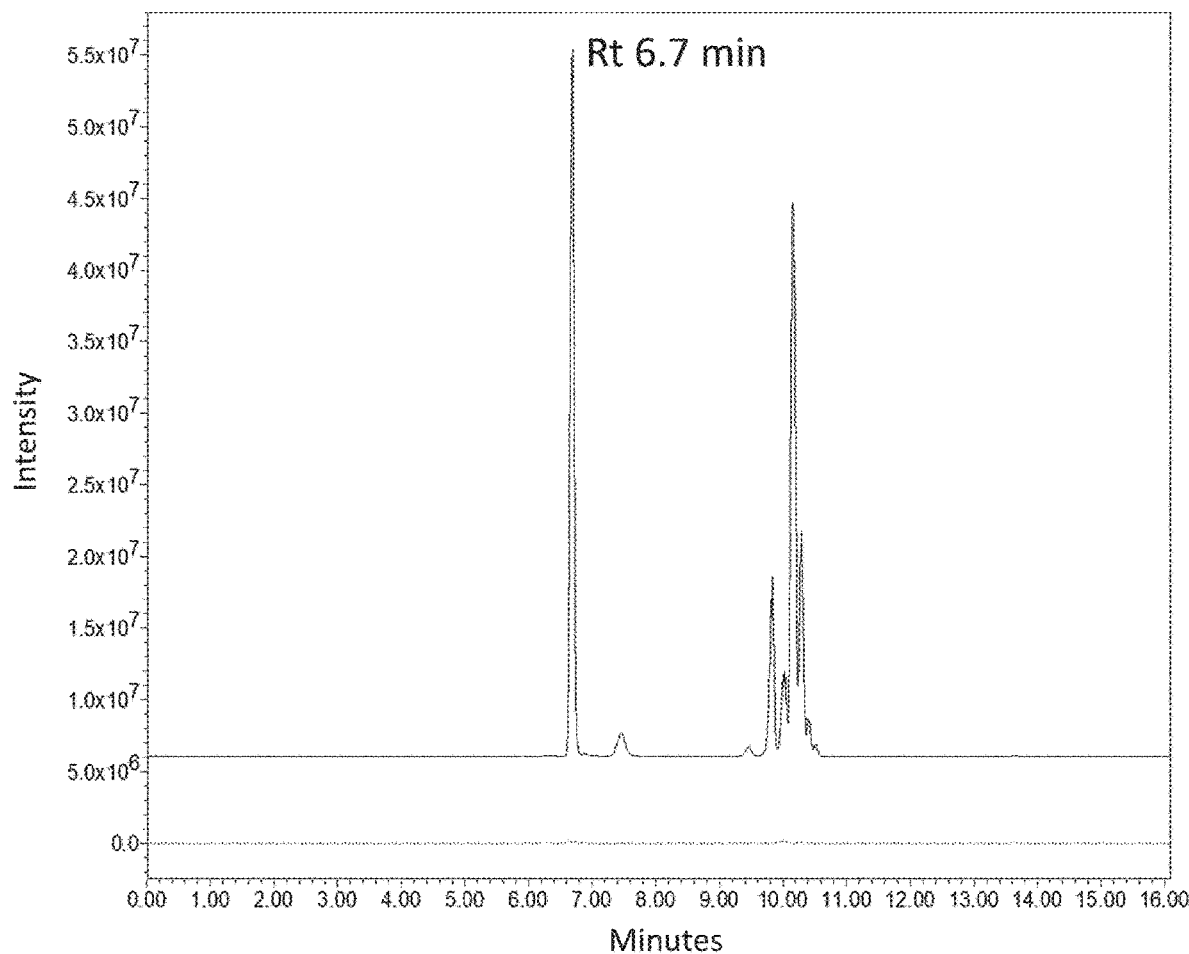

FIG. 10 shows a single ion recording in positive ionization mode at 255.3 m/z specific signal of PEG C14 for PS80 sample (dotted line) and PEG C14 (solid line). Retention time (Rt) of peak used as internal standard is given.

EXAMPLES

Materials. Polysorbate 80 was obtained from Seppic (Puteaux, France). For LC-MS, 1 g of polysorbate was dissolved in 100 mL of water in volumetric flask to give a 10 g/L stock solution stored at 2-8° C. and protected from light. Acetonitrile LC-MS grade was purchased from Fisher Scientific (Illkirch, France). Purified water from a milliQ system was used. Formic acid, polyethyleneglycol monolaurate (PEG-C12, Mn=±400 g/mol), polyethyleneglycol bis 2 ethyl hexanoate (PEG-bis C8, Mn=±650 g/mol) and oleic acid were purchased from Sigma-Aldrich (Saint Quentin Fallavier, France). PEG-C12 was used as an internal standard. PEG-C12 stock solution was prepared by dissolving 500 mg in 100 mL of acetonitrile in volumetric flask to give a 5 g/L stock solution. A working solution at 100 µg/mL was prepared by dilution in acetonitrile. Only one batch of PEG-C12 was used throughout the study. Oleic acid stock solution was prepared by dissolving 100 mg in 100 mL acetonitrile in volumetric flask to give a 1 g/L stock solution. Working standard solution for calibration purpose were prepared in a 20 mL volumetric flask with a PEG-C12 final concentration of 5 µg/mL, with varying PS80 concentration from 5 to 75 µg/mL and varying oleic acid concentration from 1 to 20 μg/mL. Added solvent consisted of a water/acetonitrile mixture (20%/80%).

LC-MS analysis. Reversed-phase separation was performed on an Acquity UPLC system equipped with a QDa mass detector from Waters (Saint Quentin en Yvelines, France). QDa parameters were set as default prior to optimization detailed here after. A zorbax Sb-Aq column (100× 2.1 mm; 3.5 μm) from Agilent (Les Ulis, France) was operated at 50° C. with a flow rate of 1 mL/min according to Christiansen et al. (*Pharmazie.* 2011, 66, 666-671). Mobile phase A and B were respectively water+0.1% formic acid and acetonitrile+0.1% formic acid. Analytical gradient was as followed: 85% A with 15% B for 1 minute followed by linear ramp to 60% B at 6 minutes held until 8 minutes before a linear ramp to 100% B at 10 minutes held for another 3 minutes followed by a return to initial conditions at 13.1 minutes for another 3 minutes. A typical mobile phase gradient is described in following gradient table:

TABLE 1

Timetable for mobile phase gradient

| | A (water) | B (acetonitrile) | C (acetonitrile + 0.1% formic acid |
|---|---|---|---|
| initial | 85% | 5% | 10% |
| 1 min | 85% | 5% | 10% |
| 6 min | 40% | 50% | 10% |
| 8 min | 40% | 50% | 10% |
| 9 min | 20% | 70% | 10% |
| 9.1 min | 18% | 0% | 82% |
| 10 min | 0% | 0% | 100% |
| 13 min | 0% | 0% | 100% |
| 13.1 min | 85% | 5% | 10% |

Analytical conditions such as mobile phase and gradient were adapted according to results obtained.

Sample preparation. Samples from biotherapeutics formulation including mAb and different excipients were used. PS80 concentration was kept at 200 μg/mL. Sample preparation consisted of a protein precipitation step with acetonitrile. To 80 μL of formulated mAb was added 20 μL of internal standard working solution and 300 μL of acetonitrile. After agitation, the mix was submitted to 10 minutes 1500 g centrifugation at 10° C. Supernatant was collected and transferred into HPLC vials. Final concentration is around 40 μg/mL PS80 and 5 μg/mL of internal standard.

Results and Discussion

Figure 1:
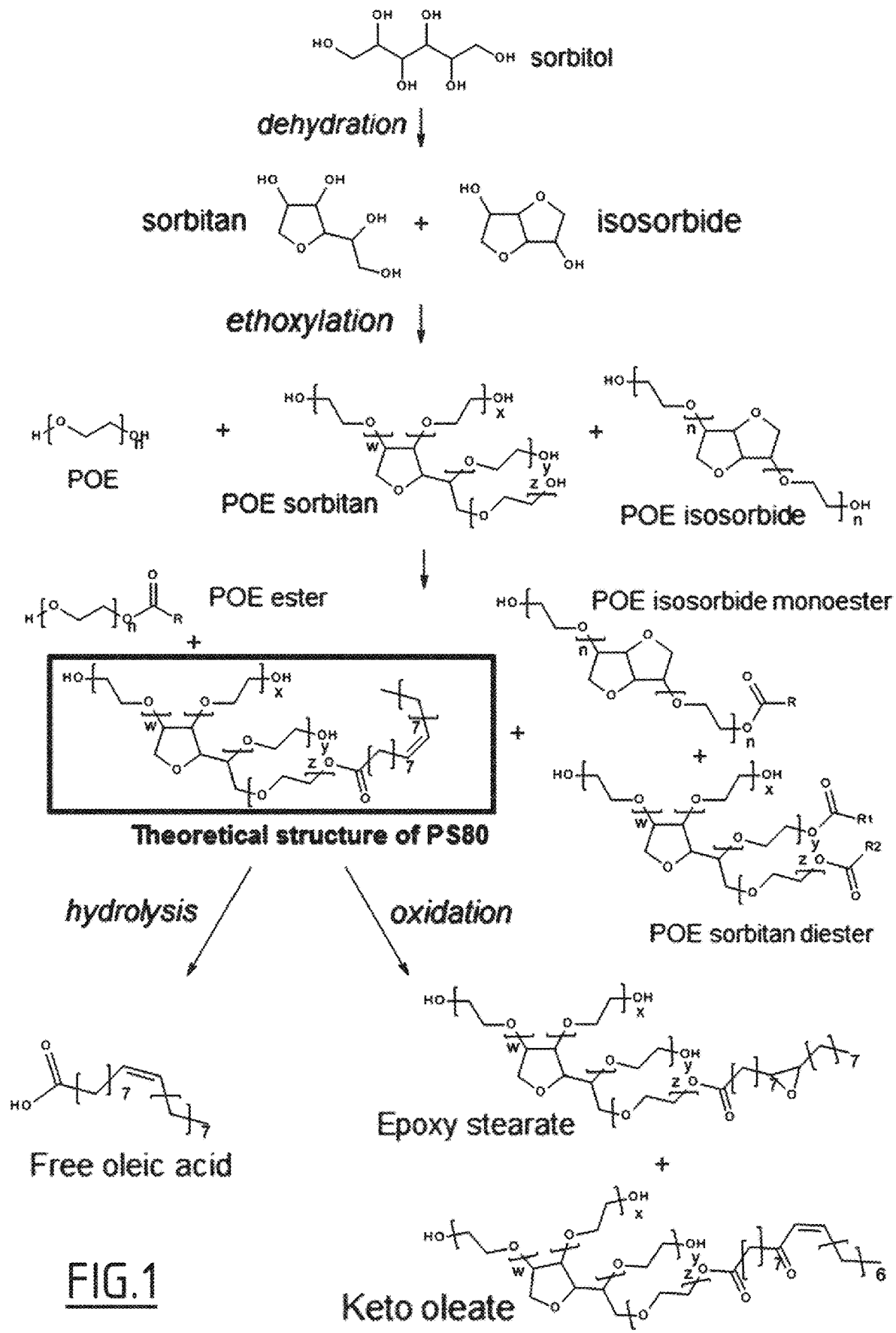
Figure 2:
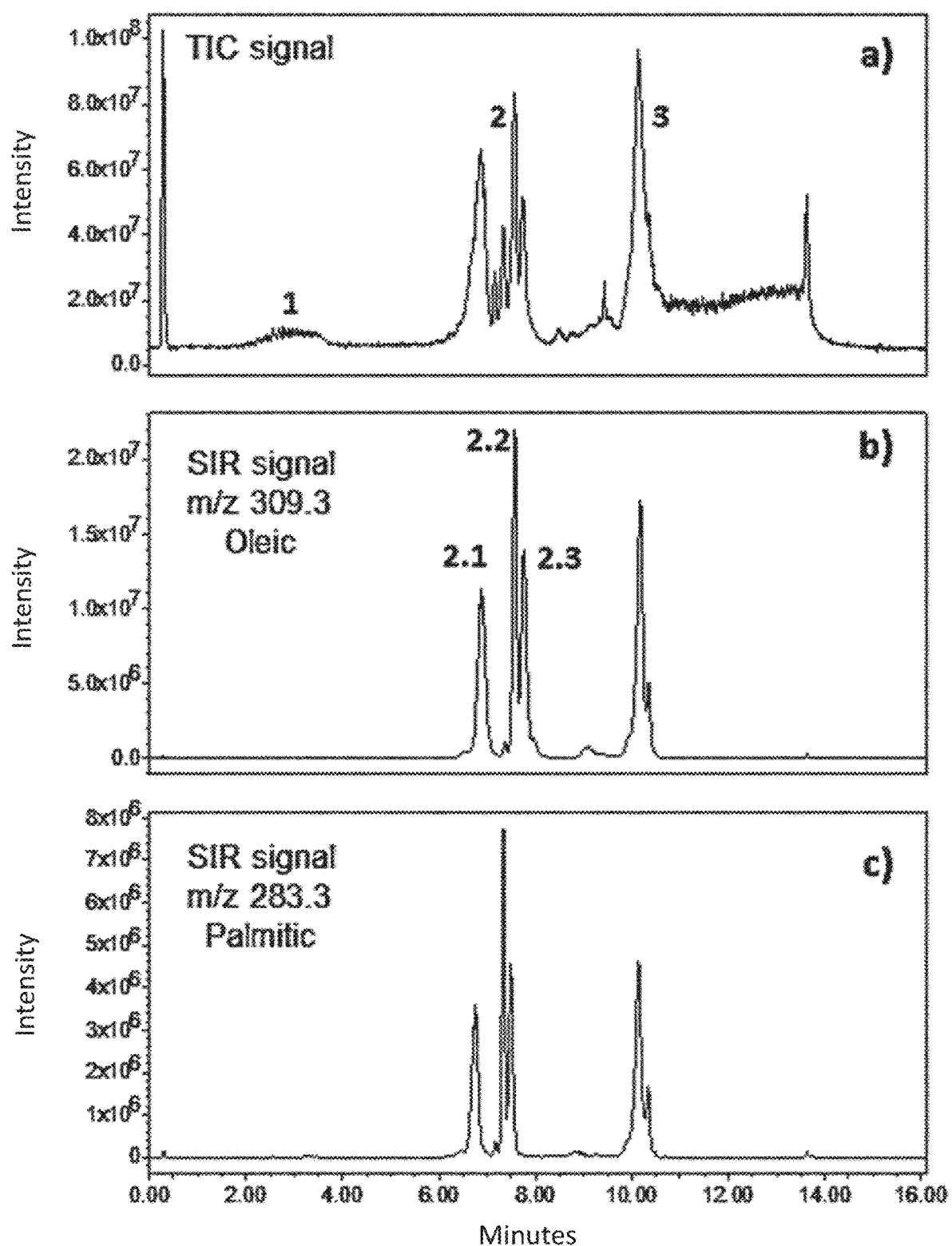

Separation of PS80 components and identification of fatty acids esters with "in source" dissociation. According to a large number of previous publications, polysorbates are heterogeneous mixture with a great diversity in chemical structure and concentration of esterified species. Moreover, nature of fatty acids involved in ester bond can vary. According to EU pharmacopeia oleic acid and palmitic acid (respectively mono unsaturated and saturated fatty acids) are the two major fatty acids of PS80. Series of low m/z ions characteristic of polyethylene glycol fatty acids ester—called dioxolanylium ion—were used to identify esterified species of PS80. Typical profile of PS80 exhibits different fatty acids ester from mono to tetra ester (FIG. 2a) while single ion recording (SIR) of m/z 309.3 and 283.3 are specific of oleate ester and palmitate ester species (FIGS. 2b and 2c). Chromatograms obtained by SIR were much easier to interpret and integrate due to the artificial gain of chromatographic resolution. Identification of the different ester species was based on work published by Borisov et al, 2015 (supra) on elution order of polysorbate species in reversed phase chromatography (FIGS. 2a and 2b).

Figure 3:
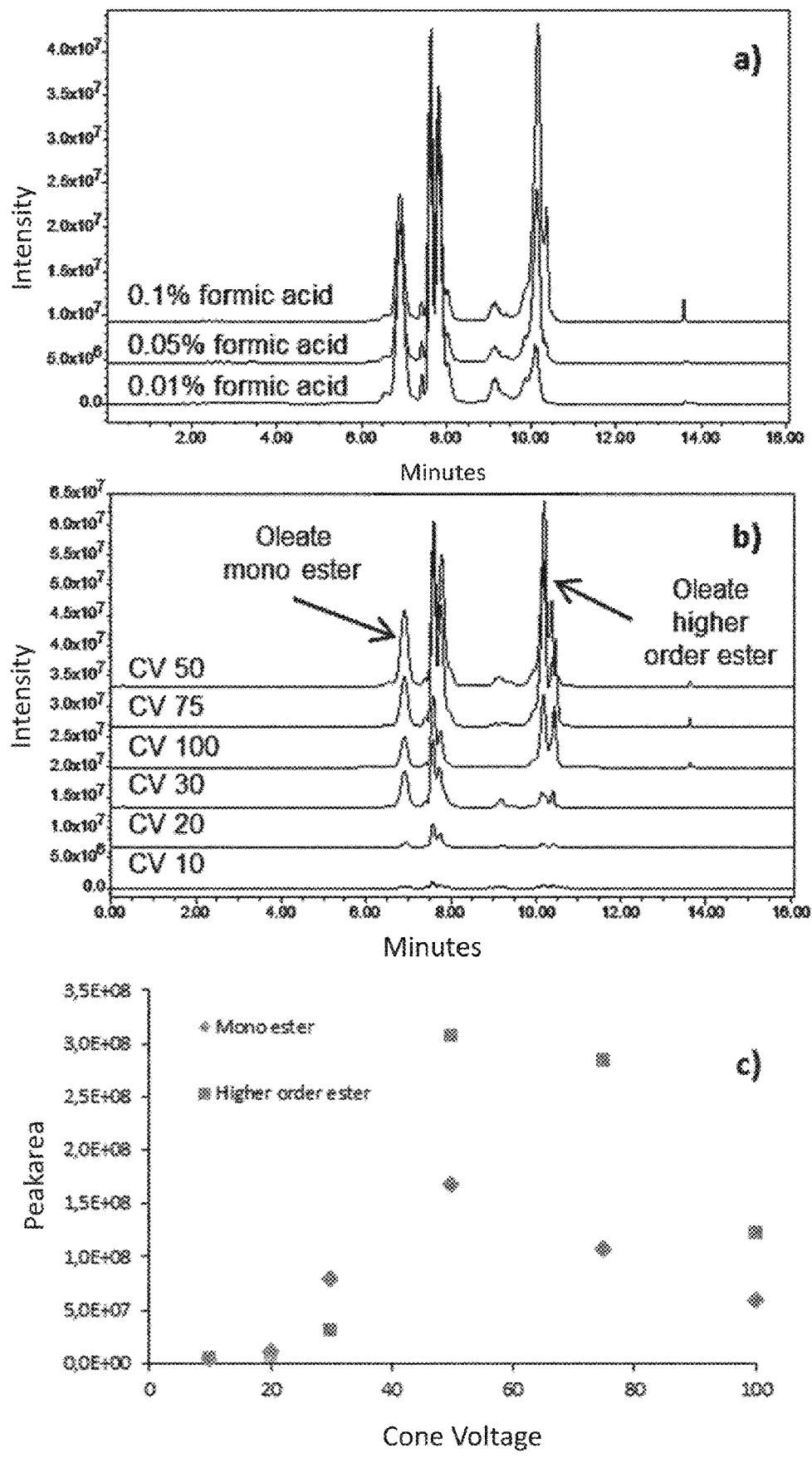
FIG. 3 represents chromatograms of dioxolanylium ions of oleate ester in positive ionization mode with various percentage of formic acid with a CV 50 (a) and with different CV at 0.1% formic acid (b). Peak area extracted from (b) is plotted against cone voltage for mono ester and higher order ester (c).

LC-MS method development. QDa is able to perform simultaneous analysis in negative and positive ionization mode for the ESI source. To gain advantage of this capability, LC-MS conditions were carefully optimized. Systematic evaluation of formic acid percentage in mobile phase and cone voltage (CV) of ESI source allowed to obtain simultaneous separation of PS80 and its degradation product with a high sensitivity. Formic acid percentage from 0.01% to 0.1% had little influence on oleate mono esters detection but was critical for higher order esters (FIG. 3a). Increased cone voltage resulted in increased signal represented by peak area of mono and higher order ester (FIGS. 3b and 3c) up to CV50. Above CV50, dramatic loss of signal was experienced. This phenomenon was explained by in source fragmentation. Increased cone voltage induced increased in source fragmentation which resulted in formation of more dioxolanylium ions up to CV50. For higher CV, intense in source fragmentation resulted in formation of secondary fragment explaining loss of signal.

Figure 4:
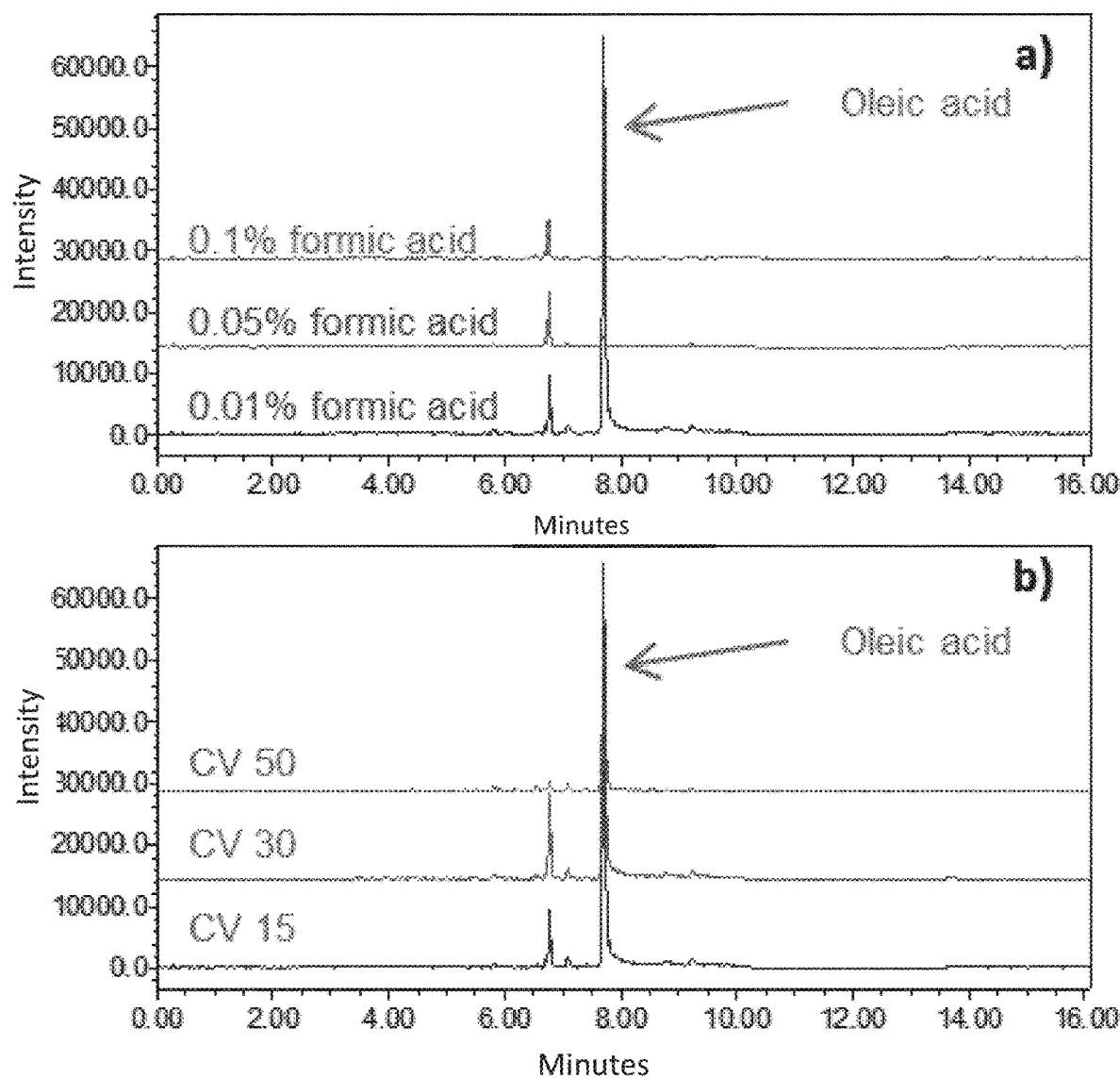
FIG. 4 represents chromatograms of oleic acid in negative ionization mode with various percentage of formic acid with CV 15 (a) and with different CV at 0.01% formic acid (b).

Detection in negative ionization mode of oleic acid required little proportion of formic acid in mobile phase—not more than 0.01% (FIG. 4a). Detection of unfragmented molecular ion of oleic acid required low cone voltage to minimize in source fragmentation (FIG. 4b). Order of elution between mono esters, oleic acid and higher order esters made it possible to put in place a ternary mobile phase gradient in order to vary acetonitrile and formic acid percentage independently throughout the analysis. LC-MS method was adapted from experimental section as follows. Mobile phase gradient with 85% A (water), 5% B (acetonitrile) and 10% C (acetonitrile+0.1% formic acid) for 1 minute followed by a linear ramp to 40% A, 50% B and 10% C at 6 minutes held for 2 minutes. Another ramp to 20% A 70% B and 10% C at 9 minutes was added. At 9.1 minutes, a switch to 18% A with 82% C was added to increase formic acid percentage to 0.1% and the ramp continued to 100% C at 10 minutes and held for 3 minutes before returning to initial conditions at 13.1 minutes. The switch between mobile phase B and C at 9 minutes was added to change formic acid percentage in mobile phase from 0.01% to 0.1% while keeping acetonitrile percentage in mobile phase on the same gradient ramp. SIR signals in positive ionization mode were recorded with CV50 while SIR signals in negative ionization mode were recorded with CV15.

Polysorbate quantification by external calibration. In previously published methods, PS80 or PS20 is quantified by using a suitable surrogate with an external calibration curve. Well known examples are methods based on hydrolysis and subsequent esterification in methanol to form fatty acid methyl ester like methyl oleate. This methyl oleate is then considered a surrogate of PS80 and quantified. Here surrogate for quantification was peak 2.1 (FIG. 2b) as this peak corresponds to POE sorbitan mono oleate which is a structure close to the theoretical structure of PS80. Based on this peak, a seven concentration levels calibration curve was constructed with concentration ranging from 5 to 75 μg/mL of PS80 in aqueous solution. Linearity was evaluated with unweighted linear regression of peak area versus concentration. Linearity was poor with $r^2$ of 0.977. Residuals exhibited a quadratic behavior explaining poor linearity performance. Repeatability evaluated by injection of 6 replicates of every calibration level was bad with RSD % of peak area above 22%. It was hypothesized that these poor results were due to competition during "in-source" fragmentation as this fragmentation is not well controlled in ESI source of the QDa, a single quadrupole.

Comparison between external and internal calibration. To overcome this issue, an internal standard (IS) was used in order to perform internal calibration instead of external calibration. Most commonly used internal standard in LC-MS for quantification purpose are deuterated compound. Given the heterogeneity of PS80 mixture this approach was not considered. Compounds with similar chemical structures and thus similar in source fragmentation pathways were chosen: polyethyleneglycol monomyristate (PEG-C14), polyethyleneglycol monolaurate (PEG-C12) and polyethyleneglycol bis 2 ethyl hexanoate (PEG-bis C8). PEG-C12 and PEG-bis C8 are commercially available (Sigma-Aldrich/Merck). PEG-C14 could not be purchased from classical chemical compounds manufacturers but was found as an impurity of PEG-C12.

As this PEG-C14 is made of PEG esterified with a C14 saturated fatty acids it was subjected to the same fragmentation resulting in formation of characteristic dioxolanylium ions at m/z 255.3 in positive ionization mode. Interferences between PS80 and PEG-C14/PEG-C12/PEG bis C8 were checked prior to using it as an internal standard. No signal from PS80 was interfering with PEG-C14/PEG-C12/PEG bis C8 signal and vice versa. Retention times of PEG-C14/PEG-C12/PEG bis C8 and PS80 surrogate peak were close, so that they underwent the same competition during in source fragmentation.

The lack of interferences of signals from PEG-C14/PEG-C12/PEG bis C8 with the signals of PS80 is illustrated by FIG. 7.

The lack of interference of signals from PS80 with the signals of PEG-C14/PEG-C12/PEG bis C8 as well as retention times of peak of interest from PEG-C14/PEG-C12/PEG bis C8 is illustrated by FIGS. 8 to 10.

For comparison purpose, internal calibration was evaluated with the same set of experiment as external calibration. Linearity was evaluated with unweighted linear regression of peak area ratio of PS80 surrogate peak over IS versus concentration. Linearity was good with $r^2$ greater than 0.999. Residuals were more or less randomly distributed and relative bias was kept below 10%. Repeatability evaluated by injection of 6 replicates of every calibration level was again good with RSD % of peak area ratio below 6% for all calibration levels. Table 2 compares these results about repeatability for both external and internal calibration with: polyethyleneglycol monomyristate (PEG-C14), polyethyleneglycol monolaurate (PEG-C12), polyethyleneglycol bis 2 ethyl hexanoate (PEG-bis C8). Comparison between these IS is based on linearity ($r^2$) and repeatability (RSD %).

methods as reported in Martos et al (2017, supra) were developed to quantify free fatty acids—including oleic acid—released by PS20 or PS80 hydrolysis.

Thanks to QDa features, SIR signal of free oleic acid (m/z 281.3 in negative ionization mode) was recorded in the same analytical run along SIR signals of intact and oxidized PS80. Oleic acid was quantified by external calibration with six calibration levels—from 1 µg/mL to 20 µg/mL—added to calibration level of PS80. For example a typical calibration level with 20 µg/mL of PS80 contained also 5 µg/mL internal standard and 5 µg/mL oleic acid. Linearity was evaluated with unweighted linear regression of peak area against concentration. Linearity was good with $r^2$ greater than 0.997 and residuals randomly distributed. Repeatability was assessed in a similar manner to that of PS80. RSD % values were between 6.0 to 13.1% with a maximum value observed for a 2 µg/mL concentration. Although RSD % values were higher than expected the assay was deemed satisfactory since this information would be used in case of investigation only. It was hypothesized that these high values were due to high baseline noise in negative ionization mode because of mobile phase composition. Indeed a compromise was made during development in favor of PS80 oleate ester species detection.

Application to formulated mAb samples. The method was applied to different cases of mAb formulation with different mAb properties and excipients but each time with 200 µg/mL PS80.

mAb1 formulated at 5 mg/mL was used to evaluate repeatability of sample preparation as well as method accuracy. Three preparations were made and analyzed on three consecutive days resulting in nine determination of PS80 concentration. Overall mean was 182 µg/mL with 3.1% RSD value. These results were in line with previous measurement with a classical mixed-mode LC-CAD analysis where a mean value of 188 µg/mL with 1.2% RSD on six measurements was found.

mAb2 formulated at 20 mg/mL was submitted to thermal stress conditions two weeks at 40° C. Results showed a drastic decrease of PS80 content from 198 to less than 25 µg/mL. More information was retrieved from other recorded signals. Chromatogram of palmitate ester species showed no difference between stressed and unstressed samples which indicates that degradation affects only oleate ester species typically observed in case of oxidation. No trace of free oleic acid was found ruling out hydrolysis as degradation pathways. SIR signals m/z 325.3 (in positive ionization mode)

TABLE 2

RSD % value of peak area (external calibration) and peak area ratio (internal calibration) for 6 replicates (except for PEG bis C8, only 4 replicates).

| | | Linearity | Target concentration (µg/mL) | | | | | |
|---|---|---|---|---|---|---|---|---|
| | | $r^2$ | 5 | 7.5 | 10 | 20 | 30 | 50 | 75 |
| External calibration | | 0.977 | 27.0 | 27.8 | 27.1 | 24.8 | 23.4 | 22.8 | 23.1 |
| Internal calibration | PEG C14 | 0.999 | 4.8 | 5.4 | 4.3 | 4.3 | 4.6 | 5.1 | 5.5 |
| | PEG C12 | 0.991 | 6.1 | 5.5 | 4.3 | 3.0 | 3.4 | 4.4 | 5.9 |
| | PEG bis C8 | 0.988 | 6.1 | 3.8 | 3.5 | 1.8 | 2.2 | 1.7 | 1.3 |

On the basis of these data, internal calibration such as PEG-C12, PEG-C14 and PEG bis C8 was shown to exhibit higher repeatability over external calibration. These internal standards exhibit similar repeatability behavior.

Oleic acid quantification. As the major byproducts of PS80 hydrolysis, oleic acid is a parameter to follow. Several showed great differences between stressed and unstressed samples (FIG. 5). Ions at m/z 325.3 were described as characteristic byproducts of PS80 oxidation either as an epoxy-stearate or hydroxy-oleate modified polysorbate. Here the whole picture of PS80 in this degraded sample was obtained with three different chromatograms recorded in one analysis allowing to conclude unambiguously that PS80 decrease is due to an oxidation.

mAb3 formulated at 50 mg/mL was another example. Samples from different batches were kept at 5° C. for almost a month before analysis. Results showed differences in PS80 content between batch A and batch B respectively 100 and 190 µg/mL instead of 200 µg/mL. This is illustrated in FIG. 6a when looking at peak 2.1, surrogate for PS80 quantification. SIR signals of oxidized PS80 revealed no difference between the batches which meant no increase of PS80 oxidation byproducts especially when compared to intensity observed in case of mAb2. Free oleic acid in solution was found in the problematic batch A at a concentration around 25 µg/mL. Only small traces of oleic acid were found in batch B (FIG. 6). Presence of free oleic acid is an evidence of PS80 hydrolysis. Given all information retrieved from this analysis, it was concluded that PS80 degradation was due to hydrolysis. As higher order esters were not impacted, it was hypothesized that this hydrolysis was from enzymatical origin.

Conclusion. PS80 is widely used in biotherapeutics formulation. Recently, growing concerns were raised about polysorbates stability in drug product and its ability to maintain its protective role against protein aggregation. Efficient methods to measure PS80 content and monitor its degradation were reported over the past few years (Martos et al, supra). Among them, LC-MS based methods showed promising results in terms of characterization and semi-quantitative information. Characteristic signals of dioxolanylium ions of fatty acids esters were used following "in source" CID to significantly simplify chromatograms and identify more easily PS80 subclasses. In previous work mentioned, their method was not verified for being quantitative. In this study, the same methodology was applied with the aim to use it for quantification at a QC level with a single quadrupole mass detector. Unfortunately first results of quantification confirmed Borisov (supra) conclusion. This issue was overcome by using a carefully chosen internal standard with similar chemical properties. It was shown that the formic acid gradient allowed for more sensitive and simultaneous detection in both positive and negative ionization mode of all compounds of interest from PS80 ester subclasses to free fatty acids.

This method was successfully applied to different cases of PS80 monitoring and especially two of them with distinctive features of PS80 degradation. In these two cases, root cause of PS80 degradation was identified using only one 16 minutes analysis. To reach out the same goal without this method it would have required three to four different methods: one for PS80 quantification (mixed-mode LC-CAD) plus one for PS80 profiling (reversed-phase CAD) along with other methods for identification of characteristic byproducts (oxidized PS80 and free oleic acid). The method presented here can efficiently replace the extensive analytical toolbox needed up to now.

The aim of this method is to provide accurate and stability indicating measurement of PS80 as well as valuable information in order to identify unambiguously root cause of PS80 degradation.

The invention claimed is:
1. A process for quantifying at least one polysorbate derivative in a sample, said process comprising:
The step of performing a LC-MS analysis of said sample based on the signal of the dioxolanylium ion;

The step of performing an internal calibration with an internal standard of said polysorbate, wherein said internal standard is an ethoxylated fatty acid of formula (I):

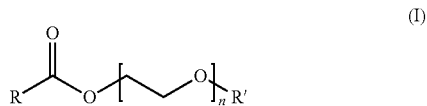

wherein:

represents a fatty acid residue;

where R represents a C3-C24 linear or branched saturated alkyl;

R' is H or

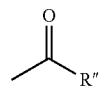

where R" represents a C3-C24 linear or branched saturated alkyl; and n is comprised between 1 and 100;

and the mixtures thereof.

2. The process according to claim 1 wherein said polysorbate is PS20 or PS80.

3. The process according to claim 1 wherein said internal standard is chosen from:

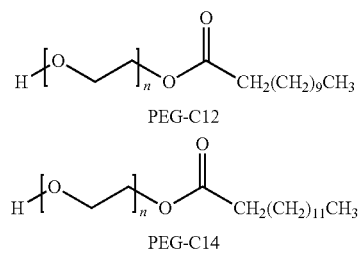

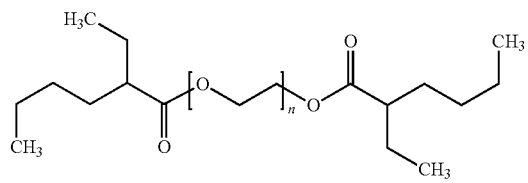

Poly(ethylene glycol)bis(2-ethylhexanoate)

where n is comprised between 1 and 100.

4. The process according to claim 1 wherein said internal standard is

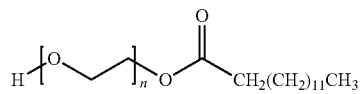

(5)

n is comprised between 1 and 100.

5. The process according to claim 1 wherein said LC-MS analysis involves a single quadrupole mass detector (QDa).

6. The process according to claim 1 wherein the LC-MS mobile phase comprises a gradient of formic acid.

7. The process according to claim 1 wherein the LC-MS mobile phase is a ternary mobile phase.

8. The process according to claim 7 wherein ternary mobile phase comprises water, acetonitrile and formic acid.

9. The process according to claim 1 wherein said sample is a biopharmaceutical formulation.

10. The process according to claim 1 wherein said sample comprises at least one protein.

11. The process according to claim 1 wherein said sample comprises at least one monoclonal antibody.

12. The process according to claim 1 wherein said process also includes the step of detecting the oxidation and/or hydrolysis of said polysorbate.

13. A process of monitoring the degradation of at least one polysorbate in a sample comprising implementing the process according to claim 1.

* * * * *